United States Patent [19]

Cherry et al.

[11] Patent Number: 5,701,894
[45] Date of Patent: Dec. 30, 1997

[54] MODULAR PHYSIOLOGICAL COMPUTER-RECORDER

[75] Inventors: Isaac R. Cherry, Mission Viejo; John A. Bachman, Dana Point; David T. Tanaka, San Juan; Hangyick So, Corona; Raphael Henkin, Dana Point, all of Calif.

[73] Assignee: Del Mar Avionics, Irvine, Calif.

[21] Appl. No.: 555,546

[22] Filed: Nov. 9, 1995

[51] Int. Cl.$^6$ ............................................. A61B 5/00
[52] U.S. Cl. ........................... 128/630; 128/668; 128/904
[58] Field of Search ........................... 128/630, 668, 128/696, 709, 710, 903, 904; 364/413.01, 413.02, 413.03

[56] References Cited

U.S. PATENT DOCUMENTS

| | | | |
|---|---|---|---|
| 4,082,084 | 4/1978 | Lipscher | 128/700 |
| 4,715,385 | 12/1987 | Cadahy | 128/710 |
| 4,892,104 | 1/1990 | Ito | 128/697 |
| 4,895,161 | 1/1990 | Cadahy | 128/710 |
| 4,964,410 | 10/1990 | Leahey | 128/696 |
| 4,967,760 | 1/1990 | Bennett | 128/715 |
| 4,974,599 | 12/1990 | Suzuki | 128/696 |
| 5,002,062 | 3/1991 | Suzuki | 128/696 |
| 5,012,411 | 4/1991 | Policastro | 364/413.06 |
| 5,086,778 | 2/1992 | Mueller | 128/696 |
| 5,111,396 | 5/1992 | Mills | 364/413.06 |
| 5,224,485 | 7/1993 | Powers et al. | 128/696 |
| 5,226,431 | 7/1993 | Bible | 128/904 |
| 5,228,450 | 7/1993 | Sellers | 128/711 |
| 5,307,263 | 4/1994 | Brown | 364/413.02 |
| 5,341,291 | 8/1994 | Roizen et al. | 364/413.02 |
| 5,355,892 | 10/1994 | Saltzstein | 128/170 |
| 5,416,695 | 5/1995 | Stutman et al. | 364/413.02 |
| 5,432,698 | 7/1995 | Fujita | 364/413.02 |
| 5,452,180 | 9/1995 | Register et al. | 361/686 |

*Primary Examiner*—Jennifer Bahr
*Assistant Examiner*—Bryan K. Yarnell
*Attorney, Agent, or Firm*—W. D. English

[57] ABSTRACT

An ambulatory physiological computer recorder that includes multiple selective plug and play signal input conditioners, a microprocessor system with operating and analyzing software and a removable memory module for data storage. The removable memory module may consist of any non-volatile memory such as IC memory, magnetic memory, optical memory or magneto-optical memory. The removable memory module used in the recorder excludes operating software; the purpose of the removable memory module in the recorder is only to receive and store acquired data. The recorder uses an alpha-numeric LCD display with control buttons for user interface to enter patient ID and recorder functional perimeters. Both operational and selective analysis software is resident in the microprocessor EEPROM memory. Software is installed in the recorder by transfer from an external source via standard serial or parallel links with applicable connectors, or by a plug-in EEPROM. The recorder includes a patient event button and audible alert transducer. The LCD panel includes a display of time-of-day and various alert or error messages. Patient physiological and demographic data that is stored, during recording and during set up in the removable memory module, is normally transferred to an external analyzer by moving the memory module to an external system, or this data can be downloaded directly via standard data links. The acquired patient data can also be formatted in a report style, either in real time or at the end of a recording to directly drive various output devices.

33 Claims, 13 Drawing Sheets

MODULAR PHYSIOLOGICAL COMPUTER-RECORDER

BACKGROUND OF THE INVENTION

1. Field of the Invention

The invention relates to the field of biomedical monitoring and analysis devices. More specifically, the invention describes a portable or ambulatory physiological, biophysical and biomechanical computer-recorder that not only has the versatile capability to monitor, record and analyze data from an ambulatory patient in real time from a variety of somatic systems and sensors, but also can in similar manner record the data on a variety of different and interchangeable memory media, and can further output recorded data in full and as analyzed to a variety of diversified output devices and media.

2. Description of the Prior Art

A variety of ambulatory physiological monitors have been in use for some time, particularly apparent monitors include among others, electrocardiograph (ECG) and electroencephalograph (EEG) as well as many others.

In Cudahy, U.S. Pat. Nos. 4,715,385 and 4,895,161, a physiological monitoring device disclosed a continuous data acquisition and processing display wherein the module may be inserted into a bedside display unit for monitoring data while reclining yet may likewise be inserted into a portable display unit via appropriate connectors to prevent loss of data in the change over from resting to ambulatory. In Ito, U.S. Pat. No. 4,892,104, an ECG monitor is disclosed that is caused to initiate data acquisition and recording in direct response to an electrical stimulation of the heart by a wave impressed upon the heart via catheter means. In Leahey, U.S. Pat. No. 4,964,410, another ECG monitoring system was conceived that utilized movable display mechanisms to more accurately measure heart rate intervals. In Bennett, U.S. Pat. No. 4,967,760, a phonocardiogram monitor is disclosed for the purpose of summarizing time dependent changes in heart sounds in a heart cycle based on spectral surfaces of a Fourier transform. In Suzuki, U.S. Pat. Nos. 4,974,599 and 5,002,062 a portable ECG unit is disclosed that includes a processing unit for outputting a display command and a responsive display unit for ECG; in the second patent, an ambulatory ECG monitor is disclosed that utilizes a removably insertable integrated circuit memory card for holding medical information for analysis and detection of ECG signals relative to specific diseases a patient may have. In Policastro, U.S. Pat. No. 5,012,411, a portable, self contained, micro processor controlled monitor is disclosed that can monitor several different ECG monitors concurrently as well as brainwave, blood pressure, blood flow, and other ultrasonic cardiovascular and intracranial data. In Mueller, U.S. Pat. No. 5,086,778, an ECG device illustrates a system for evaluating data in a two step process on recapture of the data from permanent memory. In Mills, U.S. Pat. No. 5,111,396, yet another portable ECG device is disclosed that utilizes a two way A/D-D/A system where communication is effected between a microprocessor and the ECG recording machine to flag selective time windows of successive plural-lead ECG records. In Bible, U.S. Pat. No. 5,226,431, an ECG monitoring system is disclosed wherein analog physiological data is converted to digital optical signals and thereafter transmitted to a receiver for storage from which data may be modulated for transmission over phone lines for monitoring at a distant central processing unit. In Sellers, U.S. Pat. No. 5,228,450, yet another ECG monitoring device is disclosed wherein physiological data, ECG, is temporarily stored in a buffer and thence to a magnetic disc in non-compressed form for later retrieval and analysis. In Saltzstein, U.S. Pat. No. 5,355,892, a method of recording ECG on a floppy disc is disclosed that includes both ROM and RAM for system operation and data storage with capability for adding patient information from a central system to tie up with the patient data.

In all of the varied prior art of record, there is a wide diversity of particular application of various physiological monitoring devices and recording procedures and media; however, a primary limitation of all prior art to date is that there is limited flexibility, adaptability and interchangeability of one type physiological monitor with another doing a related or similar data acquisition job, and further there is no ability to alter or change the recording/memory media for different monitoring systems requirements or environments and there is limited output capability. Indeed there appears to be yet a long standing need for a more versatile physiological monitor.

OBJECTS OF THE INVENTION

It is, therefore, an object of the invention to provide an ambulatory computer-recorder that can:

(1) record a multitude of differing biophysical/biomechanical physiological somatic manifestations with but one single recording device having interchangeable plug and play input modules for the various different physiological systems to be monitored;

(2) record data on a plug and play nonvolatile memory module that is also interchangeable via a PCMCIA interface with the recording device in order that different memory media may be utilized to satisfy differing environments and needs;

(3) utilize a plug and play micro processor/central processor unit for system operation and data analysis;

(4) provide a variety of differing plug and play outputs of recorded and analyzed data that may be provided to a similar variety of differing media;

(5) enable operator and user control, programming and event citing directly via the computer-recorder itself via coupling the unit to a personal computer;

(6) allow self sustaining and variable plug and play choice of power supply;

(7) make system and analysis firmware/software changes to the CPU with plug and play ROM and PROM modules; and (8) provide a method/process for permanently linking a patient ID number and respective patient demographic data to a unique and designated patient physiological recorded/stored data file.

SUMMARY OF THE INVENTION

The invention disclosed herein is a computer-recorder for ambulatory monitoring of a multitude of physiological processes. The computer-recorder accepts a great variety of physiological monitoring and sensory inputs enabled via a variety of interchangeable signal conditioning modules that adapt analog input signals from somatic sensors to the appropriate protocol for the microprocessor and memory requirements of the computer-recorder. Conditioned signals are then converted from analog to digital and passed to a central processor unit (micro processor) for linking, by appropriate software, patient identification and demographic data input directly into the computer-recorder or via a separate PC, to respective received and recorded data and for initial data analysis and thence to memory for recording all data input. The memory module, in like manner as the input modules, has the capacity for a variety of interchangeable memory modules including magnetic tape and disc cards, optical tape and disc cards, and integrated circuit cards (flash card). Each memory module is configured to plug into a personal computer memory card international association (PCMCIA) protocol slot of the computer-recorder as well as any other device having a PCMCIA protocol capability such as a personal computer (PC).

The C/R has additional power supply flexibility in like manner as the interchangeable and variable input and storage devices. An interchangeable power module enables a wide variety of DC power sources including various chemical batteries and solar power. Finally, in addition to multiple data input capability and multiple media memory/data storage capability, the computer-recorder also has multiple media output capability through serial and parallel ports to a modem, PC, fax, or directly to a printer for full disclosure printout of recorded data and analyzed data printout as well.

DETAILED DESCRIPTION OF A PREFERRED EMBODIMENT

Figure 1:
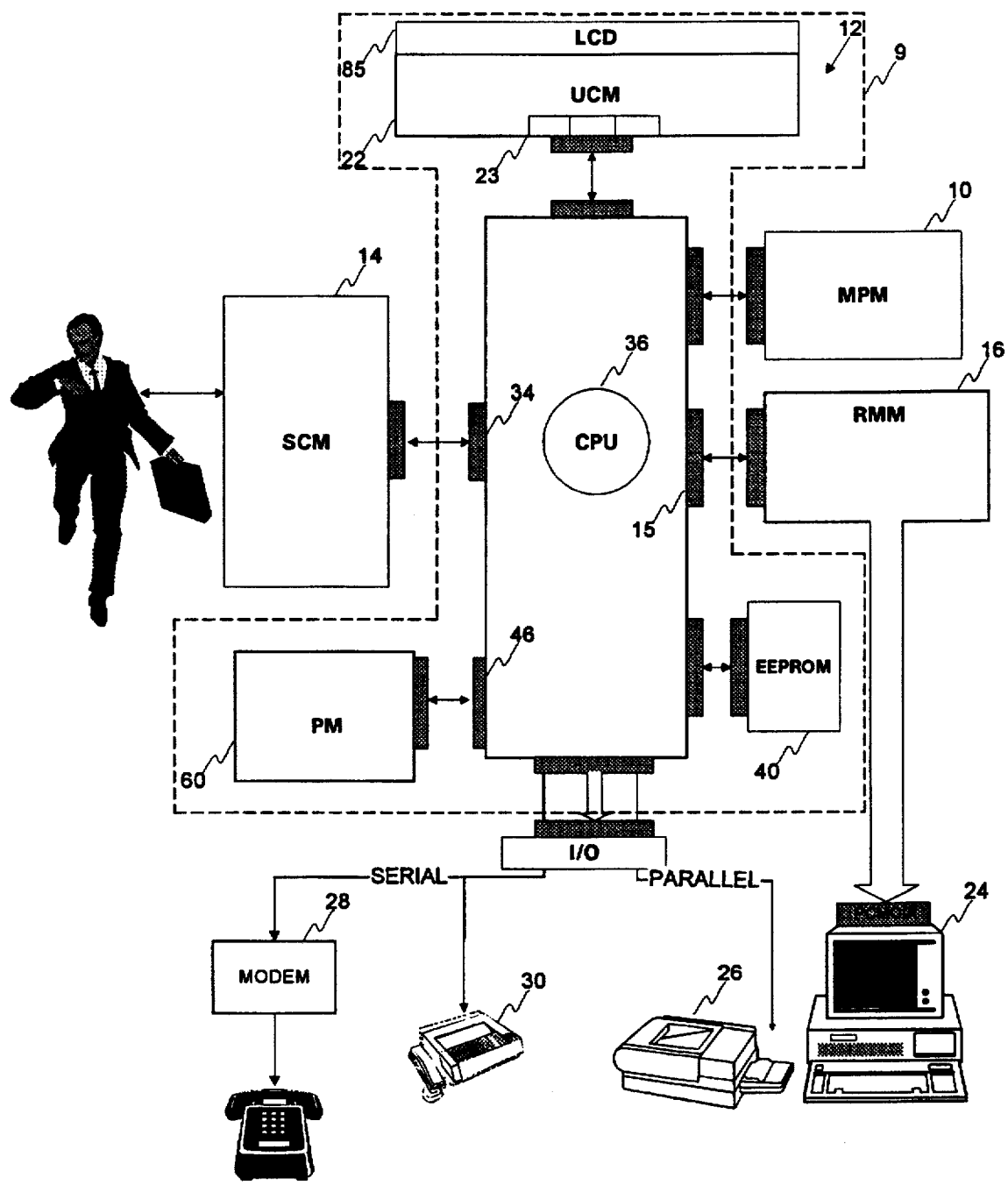
FIG. 1 is an overall, simplified block diagram of the computer-recorder system, with the main body computer-recorder delineated by a dashed line enclosure, and the multiple modular plug-in feature.

The physiological computer-recorder, illustrated in FIG. 1 and 2, hereinafter referred to as Compcorder™, described in this invention overcomes inherent problems associated with the prior art use of magnetic tape or magnetic disc media, for recording and storage of patient generated electrical potentials, commonly known as electrocardiograph (ECG) 70, electroencephalograph (EEG) 72, electro-oculogram (EOG) 74, electromyograph (EMG) 76, gastric and esophageal (pH) 78, body and skin temperature (C/F) 80, respiration ($O_2$) 82, skin conductance ($e^-$) 84, blood pressure (BP) 86, pacemaker 88 and the measurement of patient physical activity and movement (acceleration) sensors 90 to measure gravity forces. Additionally, the recorder is simple, requiring only the removal and replacement of a memory module to start new tests, and where there is no need for viewing signals on a liquid crystal display (LCD) 50, is necessary or useful. In the case of an ambulatory patient, being recorded with ECG (i.e. the Holter), no patient interaction with the recorder is required, other than a normal activation of an event button, as is done to time relate an event. In effect the recorder is a dumb recorder as it requires no patient interaction to obtain results.

The storage medium may be any non-volatile memory device, such as integrated circuit (IC) flash memory, that allows external high-impact shock and vibration influences to be ignored relative to those shocks that could disrupt the signal recording process of a storage system, that uses miniature, rotating hard disk memories. The memory device could also be any other non-volatile type memory such as recordable optical media cards, compact disc readable memory ((::DR ROM) and magneto-optical memory. The use of a removable memory medium also allows a quick transfer of recorded data to another computer, which could yield higher processing power and capability. Removable memory modules also allow immediate reuse of the recorder, by conveniently inserting a second storage medium. The storage medium is only used to store the patient identification (ID), patient demographic (i.e. vital of social statistics) information, recorder parameteres and the body generated data that was collected by the signal amplifiers. The data is stored in the storage medium, in the form of two files, one for the recorded signals and one for patient ID consisting of a proprietary configuration and includes all data from a multitude of sensors. This prevents any possibility of a mix-up of patient ID and acquired data, which sometimes happens when multiple files of patient ID, patient data, operating and analyzing software are all on the same medium. This is especially a problem for later analysis, at remote sites.

In the preferred embodiment of this invention, the operating software, for the many recording modes, is stored in read only memory/programmable read only memory (ROM/PROM) or electrically erasable programmable read only memory (EEPROM) positioned in the Compcorder™, rather than the removable memory module. This allows greater data retention reliability as has previously been offered in other systems. The software stored in ROM/PROM includes that required for the various operational modes. The software to operate the Compcorder™ can conveniently be changed by plugging in a new ROM/PROM or by downloading new software though a standard input/output (I/O) link to a PC. Selection of a particular operational mode is done by use of the Compcorder™ mode buttons in combination with an LCD display. Output of data or formatted reports can be selected at the end of a recording, to send the selections direct from the Compcorder™ to an output device such as a printer, modem or fax.

In the preferred embodiment of this invention, illustrated in FIG. 1, the removable memory module (RMM) 16 consists of non-volatile memory that has the functions of what is generally known as reading (Read) and writing (Write). Technology that can presently be used for this function is known as flash memory, which allows permanent storage during a Write operation. Written data can be erased immediately before use of the RMM again. After transfer of the RMM to another personal computer (PC) for later analysis, the memory is Read. This invention does not specifically address solid state IC memory devices alone, as other present and future optical memory devices could be used in this application as well, whether stationary or rotating including recordable compact disk (RCD) and compact disk recordable erasable (CDRE). The invention also includes the application of magneto-optical storage technology as well as any other sequential or random access storage device.

In the preferred embodiment of this invention, physiological signals that are to be monitored are selected from available "plug and play" signal conditioner module 14, which are interchangeable and removably connected to a micro processor module (MPM) 10 via a central processor unit (CPU). Each signal conditioner module 14 has a unique plug and play identification system that is read by the MPM 10 to activate the applicable recording, analysis and output programs. These signal conditioners, with various digital accuracy's, provide output either in real time or periodically, relative to an internal software algorithm. An example of this algorithm would be that multiple channels of ECG could be averaged and correlated with a previously defined correlation coefficient, which would then yield an average of the summed heartbeats. This summation reduces non-repetitive noise to low levels, below one millivolt, which then allows use of the data in the application of high resolution late potential analysis (HRLPA) on Holter ECG. The preconditioning amplifiers 14 may also include circuitry or processing power to determine the transducer characteristics relative to proper operation and to determine the proper connection of transducers/sensors to the body.

In the preferred embodiment of this invention, CPU 36 is essentially a hollow shell, assembly housing that allows insertion of and couples MPM 10, CPM 40, and RMM 16 to input/Output (I/O) ports 14 and 46. The invention's standard form consists of low power sub-miniature components, including as a minimum, the functions of control, processing, analyzing, storing, I/O interfacing, time measurement, power saving shutdown and program input from the EEPROM. The main I/O control works with a user control panel 12 consisting of an LCD alpha-numeric display 85, associated function buttons 23, and a patient event button. A power module 60, using either or both batteries and solar cells, generates the voltages necessary for all Compcorder™ functions.

In the preferred embodiment of this invention MPM 10 also has the ability to directly process and perform real time analysis of the various signals from the signal amplifiers 14. Analysis of Holter ECG late potentials can also be done as described in U.S. Pat. No. 5,205,295, wherein the ECG signals are averaged to assist in a reduction of non-repetitive noise. Another typical function of the main micro processor (MP) system is to perform real time ECG analysis using a proprietary algorithm named "DART" which algorithm is based on a Massachusetts Institute of Technology (MIT) algorithm titled "Aristotle." The DART analysis is performed on a multi-channel ECG signal, relative to: beat morphology forms, arrhythmia analysis of the Ventricular and Supra-ventricular beats, time period measurements, measurement of ST levels and formatting a report in real time or at the end of the recording period.

The present invention as delineated discloses a method and apparatus for recording medically related patient data from an ambulatory patient, into a removable memory module (RMM) 16, from a multitude of possible body related signals that can be measured. This invention details how different operational modes are selected, processed and the results transferred to the memory module 16 which is only used for the storage of patient demographic and sensor data and how it is removed from the Compcorder™ 9 for transfer to another apparatus for subsequent analysis. This type of use is refereed to as physiological monitoring and could include Holter type ECG recording in combination with other sensors or individually, however, the specific types of sensors used, nor the application, is not considered a part of this invention.

FIG. 1 shows an overall block diagram of the basic plug an play components of the preferred embodiment of the Compcorder™ 9, indicated by a dashed line, and includes five main functional modules. The functional modules include a central block, central processor unit (CPU) 36, a plug and play micro processor module (MPM) 10 which is connected to the other main modules, namely, a user control module (UCM) 12, a plug and play control program module (CPM), a plug and play signal conditioner module (SCM) 14, a plug and play removable memory module (RMM) 16, and a plug and play power module (PM) 60. UCM 12, includes a 16-character, two-line LCD display 85, and operator control switches (OCS) 22, which includes a patient event switch (PES) 23. RMM 16 is removed from the recorder after recording, then connected to a PCMCIA interface 15, in a standard PC computer 24, that may be of the IBM PC or Apple Mac type. Using standard software in the Compcorder™ 9, the stored data is transferred to PC 24 for later analysis using standard Holter programs. Compcorder™ 9 has standard output connections to allow the transfer of data or reports to other devices as well such as printers 26, modems 28 or fax 30. Selection of these outputs is made before RMM 16 is removed from the Compcorder™ as described in the user control module 12 descriptions.

Figure 2:
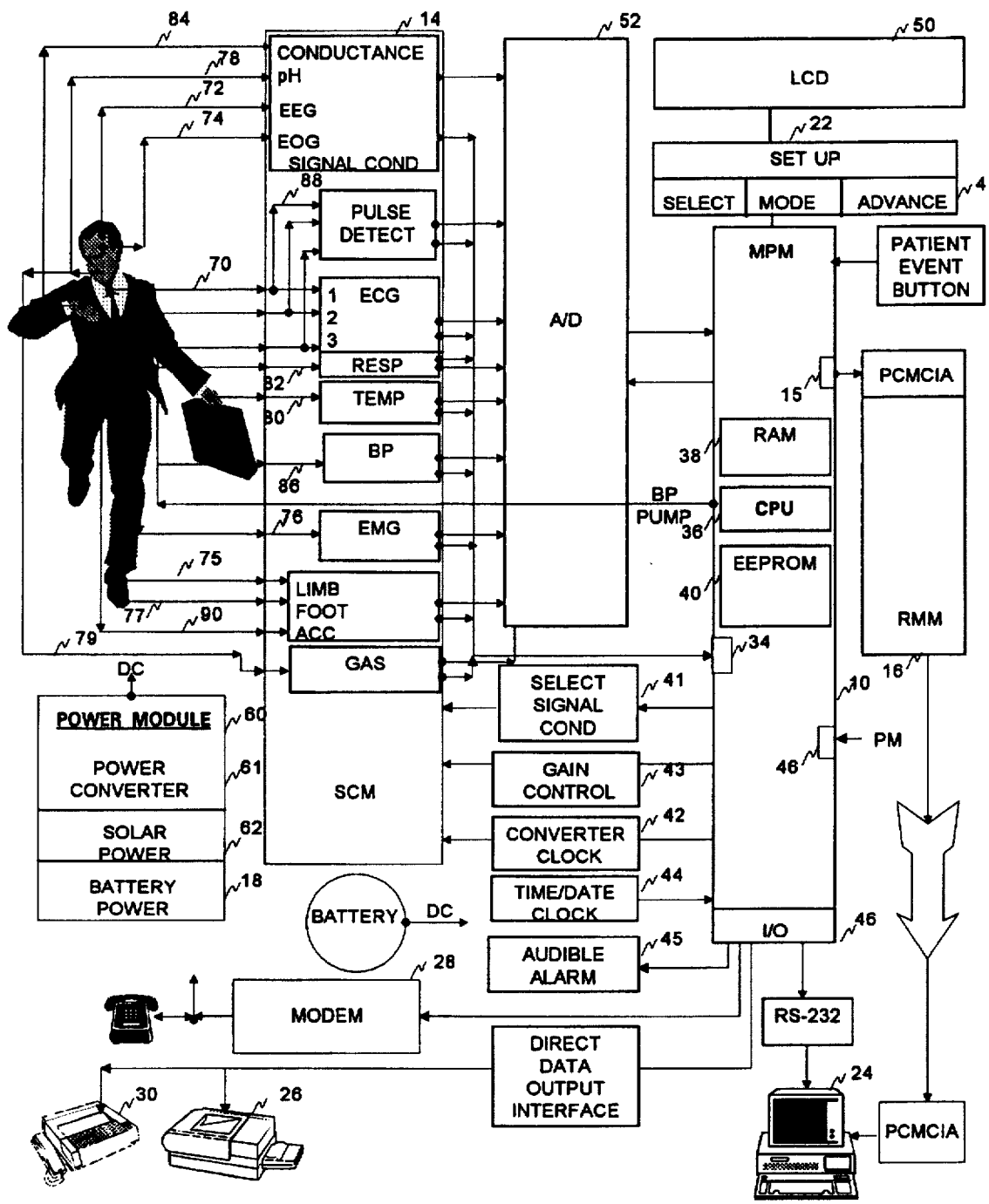
FIG. 2 is an overall, detailed block diagram of the computer-recorder system.

A more detailed diagram of Compcorder™ 9 system is shown in FIG. 2, and includes details of the types of signal conditioning modules (SCM) 14 used in this application. The design includes the ability to plug in different types of signal conditioning modules 14, into a keyed main printed wiring board 34, wherein each module is identified as a "plug and play" module 14, which sends identification to the main processor (MPM) 10, to distinguish the input function. After identification of the module 14 type through a signal select conditioner 41, MPM 10, allows an associated program to be activated.

The central processor unit 36 shown in FIGS. 1 and 2, includes a low power micro processor module 10, interconnected with conventional IC circuits consisting of RAM memory 38, ROM/EEPROM memory for CPM 40, timers 42, time/date IC's 44, gain control 43, electrically erasable memories (EEPROM) and conventional I/O input/output circuits 46. These items may be separate functional items or may be part of CPU 36. The ROM and EEPROM for CPM 40 memories perform similar functions of storing the operational programs. Operational basic programs that control standard operation are stored in the plug-in ROM devices 40. Patient demographic data input to the recorder, either from the user control module 12, set-up switches 22, or from an external source, such as a PC 24, is stored in EEPROM 40, which is electrically erased at the start of each new recording session.

Power shut down operation of the CPU 36, is an essential operation of this invention, during idle processing periods, to save battery life and extend the recording time by at least two times under a full load of signal conditioning modules 14. Depending on the amount of signal conditioning modules 14, in use for a given test, it has been shown that the total battery 18 current used has been reduced as much as from 60 ma to 12 ma. Power saving uses the software instruction "stop". When the stop instruction is executed, CPU 36 oscillator is stopped, all internal CPU 36 registers are retained and all refresh operations are STOPPED.NMI or "reset" inputs will terminate the stop mode. During recorder setup the CPU 36 stop mode is interrupted every 250 milliseconds to service the push buttons 48 and update the LCD display 50, then the CPU 36, returns to the stop mode. Wake-up time is about 0.2 milliseconds.

During recording, the stop mode is interrupted each time any of the analog digital converters 52, makes a conversion, approximately every 8 millisecond's at 128 samples per second. The sample is stored, some housekeeping is performed and CPU 36 is put in the stop mode. CPU 36 is out of the stop mode for 0.9 milliseconds for this process. LCD 50 is also updated once per second. On these wake-ups CPU 36 is active for 1.5 milliseconds. The sampled data is stored in a buffer of static RAM 38. Every ten minutes the static RAM 38 samples are combined with the patient demographic data and results are transferred to the RMM 16, via a PCMCIA protocol interface 15.

The micro processor module (MPM) 10 is also capable in one of the operational modes to simultaneously perform signal averaging of ECG Holter type signals for the purpose of lowering the non-repetitive noise to assist in the use of measuring late potentials, as defined in U.S. Pat. No. 5,205, 295. In this application, ECG signals from three channels are averaged in real time continuously or in periods, creating a high-resolution digital equivalent to reduce the associated signal/noise to less than one microvolt, the details of which were shown in the referenced patent. The resulting digital average for the averaged periods is then stored in the RMM 16, in a file with other patient data, either in real time or at the end of a recording period.

The RMM 16, recording medium is of a standard type known as non-volatile memory, emulating the characteristics of flash memory. RMM 16 requires minimal preparation after manufacture other than to format the medium in an industry standard, disc operating system (DOS) format, or any other format, random or defined, suitable for this application and to have one blank file placed on RMM 16 as a contiguous file, which will collect the ECG data. Formatting is normally done by the supplier of the RMM 16 or by the use of a PC 24 with a PCMCIA 15 port and utility software. If the recording media has been used, it is automatically erased before more data is recorded. No operational or analysis programs are resident on the memory module 16 in this invention. Programming is selected by the program options in the Compcorder™ from PROM and EEPROM 40 memory, using the push-button switches 48. In this embodiment of the invention, removable memory module 16 is only used to receive data and non-volatile memory 16 is only used to store physiological and relevant ID data.

FIGS. 1 and 2 illustrate the present invention, employing a memory module 16, which may be of any type that emulates the functions of non-volatile memory, in that the memory module 16 retains data while it is in the Compcorder™ 9 as well as when module thereof is removed from the Compcorder™ 9, i.e. memory module 16 continues to hold the data without being refreshed. In this embodiment, the same memory 16, or a similar memory module 16, is re-used for the next recording. Memory module 16 has the ability to be erased of any previous data stored, either by external means, or in the Compcorder™ 9 prior to re-recording. Memory module 16 can be easily obtained in the market, are economically available and can emulate the foregoing functions generically called flash memory module 16; however, other optical cards, optical disks, magneto-optical disks and IC RAM cards with or without separate batteries could also perform these same functions, now and in the future.

A further novel embodiment is that the physiological Compcorder™ 9 disclosed herein generates two files that can be used by an external PC computer/analyzer to store and/or analyze the data by connecting the two files, i.e. a patient ID/demographic security file and a patient data file and/or a patient digital data file. Therefore, no mix-up can occur between these two files when they are transferred to the external PC 24 for analysis. This will ensure that, in both the physiological Compcorder™ 9 and the in the external PC analyzer 24, a patient identification number entered by the operator belongs to that patient whose stored digital data is on removable memory module 16. The patient ID number is entered either into the Compcorder™ 9 directly or into the PC/analyzer 24 first, and then into the Compcorder™ 9. This ID number and other patient demographic data along with the event/test data is stored in a special file called SECURITY.NMS in the RMM 16 of the Compcorder™ 9 and checked against the ID number entered into the PC/analyzer 24 at download time. If a conflict exists, the operator is alerted by audible alarm output 45 and must resolve the conflict before the EGG data in the Compcorder™ can be copied into the PC/analyzer 24.

The non-volatile, removable memory module 16 must be prepared before use in the Compcorder™ 9. The module 16 is formatted and has one, active partition which may be as large as the capacity specified by the manufacturer of the module. A special file, which we will call SIGNAL.DAT, for purposes of this disclosure, is recorded on the RMM 16, to reserve contiguous file space for raw data from signal conditioners 14. No data is recorded into the above file, other than a non-defined character for each byte. For Holter ECG data, this file must be as large as the largest file that is expected to be recorded. The size of the file is typically 33 megabytes for a 24-hour, three-channel recording using an analog and digital A/D converter 52 of 128 samples/second (s/s) and 8 bits. No other pre-conditioned files are required to begin a recording, with the exception that room on the RMM 16 must be available to record the SECURITY.NMS name file including the patient ID and patient event data when the Compcorder™ 9 is started. For recording at 256 s/s with 8 bits, the size of the memory would be 66 megabytes for the same recording length. For recording at 1024 s/s and 12 bits, A/D resolution this size would be proportionally larger depending on the time of the recording.

The entering of patient ID data into the Compcorder™ 9 can be done in two ways. The subsequent verification is done in the PC/analyzer 24. One method would be when the patient ID is entered into the removable memory module 16, directly from the Compcorder™ 9 for patient information prior to hook-up of the Compcorder™ 9 to the patient. The other method is when the removable memory module 16 information is downloaded from the PC analyzer 24 prior to patient hook-up for EGG or other physiological recordings.

When RMM 16 and removable battery 18 have been inserted into the Compcorder™ 9, Compcorder™ 9 first performs self tests and then checks for the presence of valid, patient information files on the RMM 16. In one of the cases described above, with no downloading before recording, a PC computer 24 will not find a patient ID number. In this case, the Compcorder™ 9 and LCD 50 will show the patient ID input on display 50 with a cursor at the first character ready to input the patient ID number. A correct patient ID number is normally entered at this time. However, the foregoing screen can be bypassed at this time by pressing the mode 93 button, FIG. 3, before any data is entered. The recording cannot be staffed until this display is re-entered and a patient ID number is entered. This number is stored in the special patient ID/event dual file, SECURITY.NMS, in the RMM 16.

If the patient ID information is entered into an external PC analyzer and downloaded into the RMM 16 before the recording, the recorder LCD 50 display will show the patient ID number entered into the PC analyzer 24. This will be shown immediately after the Compcorder™ 9 self-test is completed in place of the patient ID input display 50. The LCD 50 display tells the operator to press mode 93, FIG. 3, to accept this number. If the mode 93, FIG. 3, button is pressed, the recording can be staffed from the appropriate display. If any other button is pressed, the patient ID entry display appears and the operator must enter a patient ID number or a recording cannot be staffed. This implies that the operator did not accept the number shown and has entered the correct number. This correct number is stored in the same SECURITY.NMS ID event file for later comparison with the number entered into the external PC analyzer 24.

In the external PC analyzer 24, the next step is to ensure that no mix-up of the SECURITY.NMS ID event file and recorded digital data in the SIGNAL.DAT file, has been made when a transfer of the RMM 16 is made from the Compcorder™ 9 to the PC analyzer 24. At the end of the recording, the RMM 16 may be taken to the PC analyzer 24 for downloading and analysis of the recorded data. During the download process, recorded data is checked on the PC analyzer 24 which displays that the recorded digital data being downloaded, belongs to the patient, with the respective recorded patient ID number.

Before the recorded digital data can be transferred from the RMM 16 to the PC Analyzer 24, the patient ID number, entered into the Compcorder™ 9 or accepted before recording began and stored in SECURITY.NMS as described above, is compared against the ID number entered into PC analyzer 24. If the numbers do not compare, a screen on the PC analyzer 24, prints a message and displays the two different patient ID numbers so that the operator can resolve the conflict. The operator is asked to accept either of the two displayed numbers or to enter a new patient ID number. Once the conflict is resolved, the transfer of the recorded data will be completed.

The removable/interchangeable power module (PM) 60 contains circuits 61 to convert battery 18 power to the voltage required by the various circuits in the other four modules. The number of batteries 18 used and the type depends on the expected test duration. The design of the circuits in power module 60 allows alkaline type batteries 18 to be added in parallel, extending the life as a function of the number of batteries 18 used. Batteries 18 may be either single-use types or re-chargeable types. Batteries 18 for single-use, are removed from the Compcorder™ 9 prior to the next use. The re-chargeable batteries 18 can either be recharged in the recorder or through an external source. The Compcorder™ 9 also has the capability to be charged or operated from solar cells 62 that is connected through the 46 connector. This capability assists in an extended multi-day use, in an outside environment, or where no replacement or fresh batteries 18 are available.

The SCM 14 is detailed in the physiological Compcorder™ 9 system block diagram of FIG. 2, as described in this embodiment. SCM 14 includes the necessary sensors that are attached to a patient and may include electrodes for ECG 70, EEG 72, EOG 74, EMG 76, blood pressure 86, esophageal pH 78, temperature of skin or body 80, respiration 82, skin conductance 84, pacemaker 88, spikes and may include body and limb sensors 75 measuring body position, physical activity, body movement, body and limb position/orientation, foot force 77 and acceleration sensors 90. Most of these terms and processes have been known in the art for many years. Applicable sensors are attached in single or multiple functions and are selected for use under program control by respective switches on user control module (UCM) 12, as applicable for the test.

Figure 3:
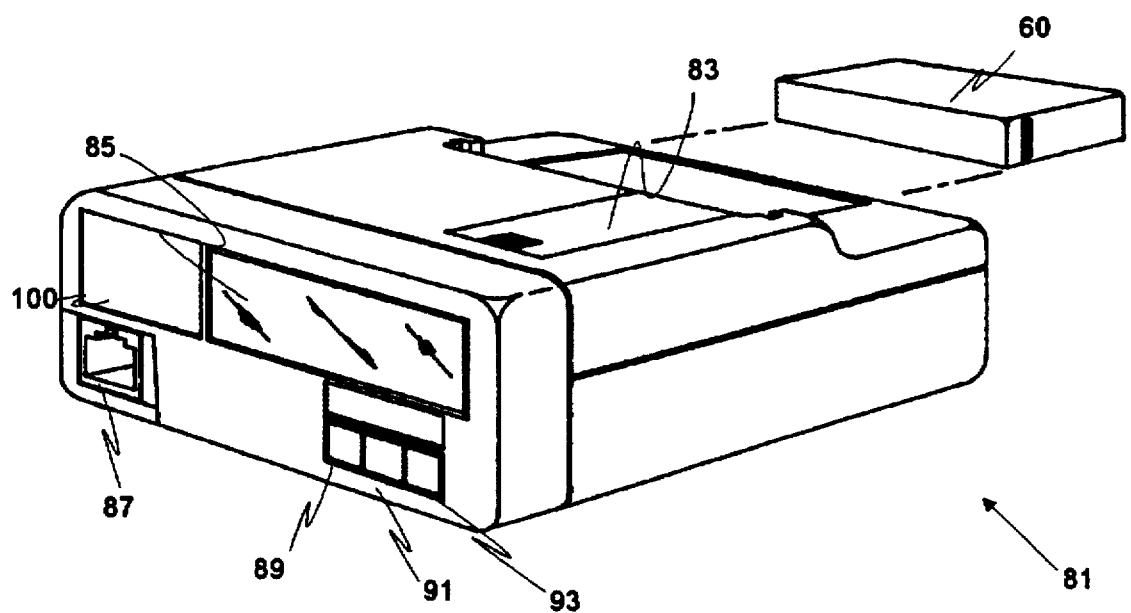
FIG. 3 is an overall perspective view of the mechanical structure of the computer-recorder, illustrating the plug and play power module feature.

As illustrated in FIG. 3 the Compcorder™ unit 9 is encased within a miniature housing 81 made of plastic and other durable parts to handle a rugged ambulatory outside environment. Compcorder™ 9 is of a convenient size and shape to be worn on a patient's belt with a suitable case or in a pocket.

FIG. 3 illustrates a perspective view of Compcorder™ 9, with the removable battery compartment 83 on the top and interchangeable power unit 60 slidably inserted. Front panel 100 consists of a two-line alpha-numeric LCD display 85, signal input connector 87 and three (3) buttons marked select 89, advance 91 and mode 93. Any one of these three buttons may be pushed by the user to indicate an event.

Figure 4:
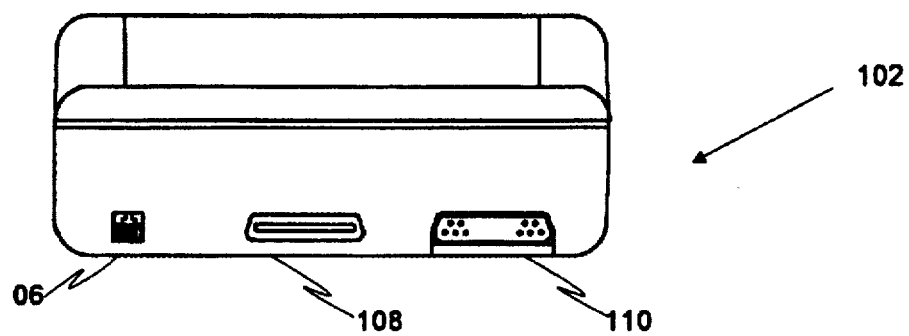
FIG. 4 is a rear end view of the computer-recorder illustrating the various outputs, hence the multiple output capability feature.

FIG. 4 illustrates a view of the rear section of the Compcorder™ 9 housing 81 illustrating a modem output 106, a printer-fax station 108 and an RS 232 link 110.

Figure 5:
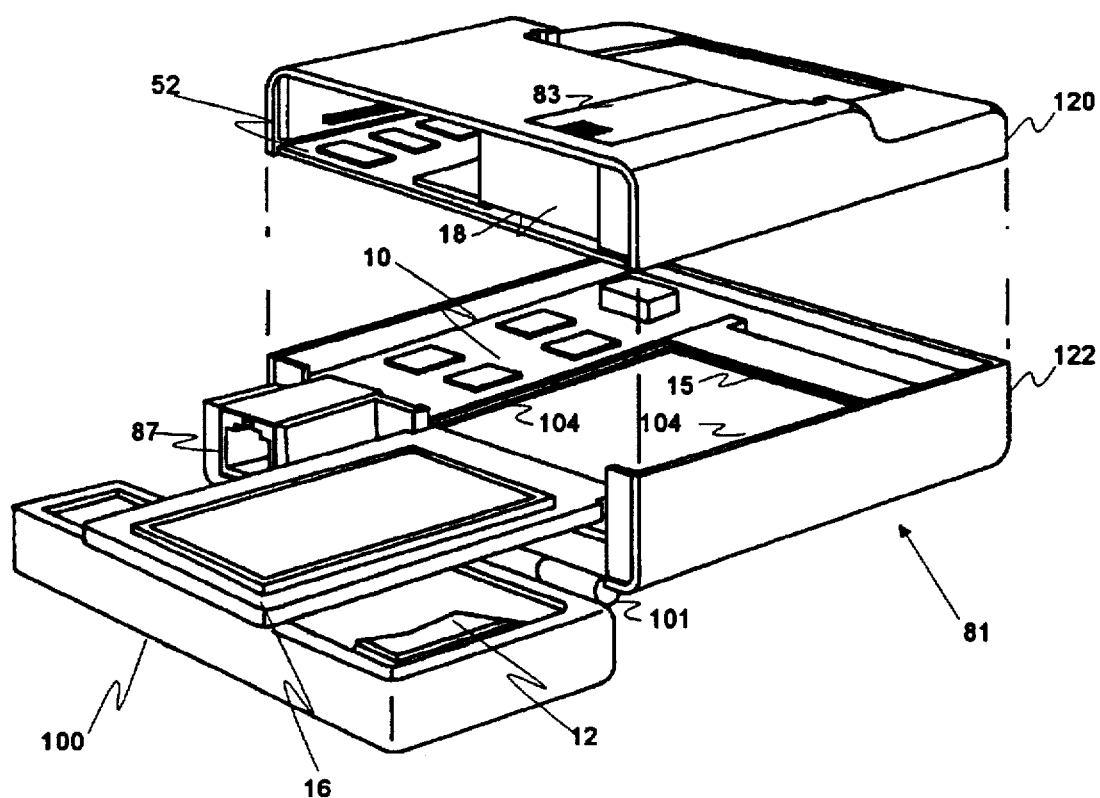
FIG. 5 is an open door and exploded perspective view of the computer-recorder illustrating the removable/interchangeable memory media capability feature.

FIG. 5 illustrates an exploded perspective view of the upper 120 and lower 122 enclosures of Compcorder™ 9 housing 81 with the front panel 100 folded down and open from a hinge 101. FIG. 5 also shows the location of where the RMM 16 is plugged into the Compcorder™ 9. Removable module 16 is simply inserted into the slot provided along guide tracks 104 into a personal computer memory module international association (PC MCIA) connector/interface 15.

Figure 6:
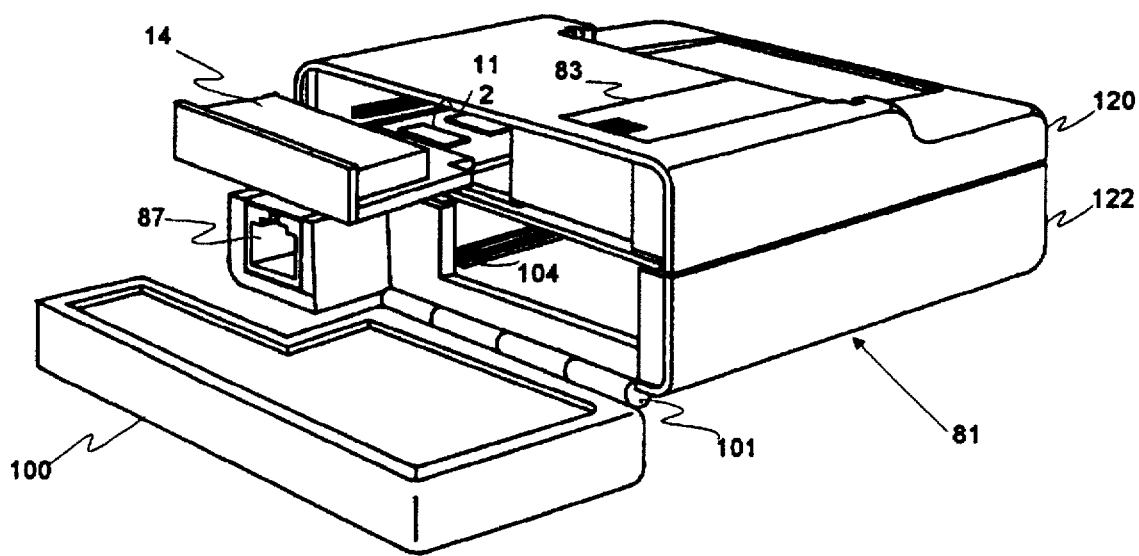
FIG. 6 is another open door view of the computer-recorder illustrating the removable/exchangeable input signal conditioner module, hence the multiple input capability feature.

FIG. 6 illustrates an inside perspective of housing 81 with opened panel 100 illustrating the electronic assemblies therein with a typical plug-in signal conditioning module 14, which is connected to the front input signal connector 87 via a motherboard 112. The plug-in module 14 is of the plug and play type that includes built-in module identification of name, part number and revision, which is stored on a PROM.

Referring again to FIG. 3 the user control module (UCM) 12 is fully disclosed in the Compcorder™ 9 outline drawing. The Compcorder™ housing 81 is configured with several battery compartment 83 sizes that can accept different types and numbers of batteries 18, such as alkaline, nickel metal hydrate or nickel cadmium but not necessarily limited thereto. The size and type of the batteries 18 to be used, is selected depending on the duration of the test proposed. FIG. 3 illustrates the UCM 12 push-button switches 89, 91 and 93. LCD 85, alpha-numeric line viewer, enables the unit to be set up relative to what specific test is to be recorded including the entry of patient ID and demographic information. It should be noted that LCD 85 display is not intended to display the continuous sensor analog graphical signals such as ECG.

The push-button switches 89, 91 and 93 are accessible to the operator and are labeled mode 93, select 89 and advance 91. Switches 89, 91 and 93 are used by the operator to step through the menus, select the sub-menus and select items on sub-menus for execution and storage. During all phases of this user interface, the mode 93 button changes to the next main menu. The select 89 button selects the function to be activated or changed under the main menu. Once the selection is made the cursor moves to the next selection. The advance 91 push-button advances through the selection choices at the cursor or the data options on other selections. Set-up switches, 89, 91 and 93 are also used as patient event buttons once the actual recording is started. Pushing any of the aforementioned buttons inputs into the memory the time of the switch closure.

Figure 7:
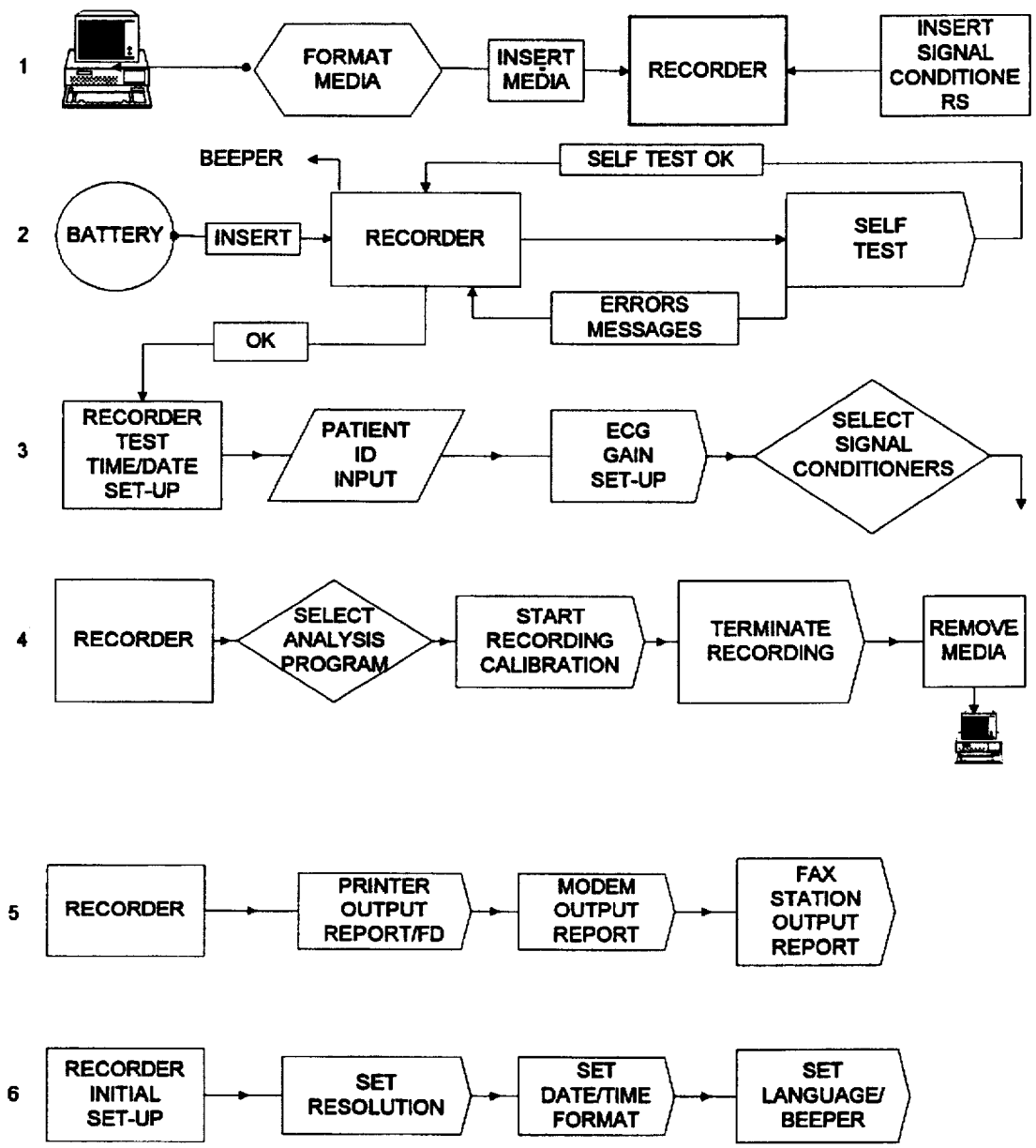
FIG. 7 is a block flow chart indicating the computer-recorder set up and operating procedure.

FIG. 7 illustrates a block flow diagram of an overall operational flow chart which illustrates the sequence of user operation before attachment of the Compcorder™ 9 to a patient. This sequence is broken down into six separate descriptions; namely, (1) RMM module 16 and signal conditioner module 14 insertion; (2) battery 18 insertion and self test; (3) recorder set-up of ID input, gain set 43 and selection of signal conditioning 41 programs; (4) analysis program selection, recording start, termination and RMM 16 media removal; (5) physiological output PC/analyzer 24, reports to printer 26, modem 28 and fax 30; and (6) Compcorder™ 9 initial set-up of resolution, date/time format, language, and audio beeper and select foreign language other than English to be used.

Figure 8:
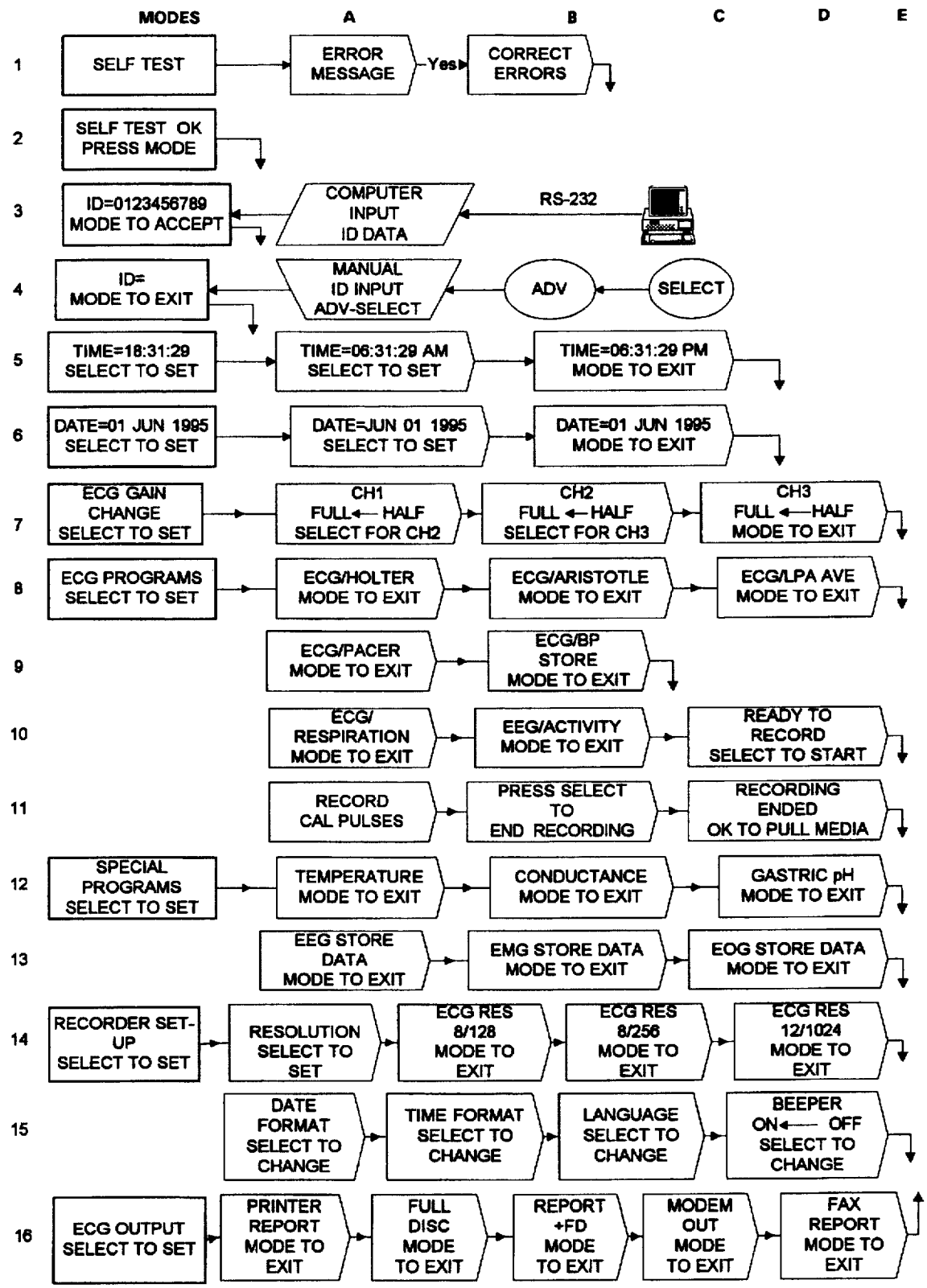
FIG. 8 is a block flow chart of computer-recorder programming process with actual LCD message.

FIG. 8 shows a chart of the LCD 85 messages displaying information and command requests. The following is a detailed description of the messages displayed to the operator on the LCD 85 and the responses to battery 18 insertion, RMM 16 insertion and pressing the three (3) push-buttons, mode 93, select 89 and advance 91. On occasion, audible feedback is provided by the audible beeper 45. LCD 85 display #1 shows an arrow on the bottom line that moves across the display to show the test is progressing. RMM 16 is inserted into the Compcorder™ 9 prior to inserting the batteries 18.

Self-test occurs upon insertion of the batteries 18. LCD 85 is as shown in the flow chart #1. At the completion of the self-tests, the display is as shown in #2. If one of the self-tests fail, an error message is shown on the LCD 85 and audible feedback is provided by a piezoelectric beeper 45. When the mode 93 button is pressed, the first menu of the Compcorder™ 9 initialization, as shown in #3, is displayed. This is the patient ID input display. The patient ID input begins when the self-test is complete and the mode 93 button is pressed. LCD 85 will show the display shown in #3 or #4. Patient data can also be downloaded to the Compcorder™ 9 from an external PC computer 24 at the start of a test by the selection of external input as shown in #3. Advance 91 and select 89 buttons must be used to enter the desired patient ID number.

During patient ID entry, the advance 91 push-button will increment the digits at the cursor position and the select 89 button will move the cursor to the next position. When the cursor reaches the last position, the next press of select 89 will move it to the first character of the patient ID number. A minimum of one and a maximum of 11 characters can be entered. When the mode 93 button is pressed, the displayed patient ID number is stored and the display changes to #5. To insure that the subsequent recording is properly identified, a patient ID number must be entered following a power-up. If a new number is not entered, the subsequent recording cannot be started. If a new number is entered and the batteries 18 have not been removed, subsequent entries into this display can be used to edit the patient ID number. Patient data downloaded from an external computer 24 will show the patient ID number on the LCD 85. If this number is correct, the operator presses the mode 93 button and this number will be accepted and the time display seen in #5 or #5A will be shown. If the select 89 or advance 91 button is pressed instead of the mode 93 button, this indicates that the displayed patient ID number is not accepted and the patient ID input display shown in #4 will again be seen. A new patient ID number must be entered as described above. If the select 89 or advance 91 button was pressed and if you wish to see the patient ID number that was entered at the external computer 24, you can restart the Compcorder™ 9 and re-display this number by removing and replacing the battery 18.

The time of day display, as shown in #5 or #5A (either a 12 or 24-hour clock), is displayed when the patient ID entry screen is exited by pressing the mode switch. The display is in hours, minutes and seconds. The display is a 24-hour or 12-hour (am/pm) clock format as determined by a Compcorder™ 9 set-up display selection. A 12-hour am/pm display is shown in #5A. If the time of day displayed is correct and does not need to be set, pressing mode 93 will display the date as shown in #6. If time of day is to be set, pressing select 89 will present the display shown in #6B. The cursor appears under the first character capable of being changed. The advance 91 push-button will increment through the possible characters in each position. Pressing select 89 button will move the cursor to the next position. When the cursor reaches the last character, the next pressing of the select 89 button will move the cursor to the first time of day character. When the time of day display is correct, pressing the mode 93 button will show the date display shown in #6B.

The date display as shown in #6 will appear when the mode 93 button is pressed and when the time of day is being displayed. The date display will be of the day-month-year or the month-day-year format as shown in #6 or #6A, respectively. The date format is determined by the Compcorder™ 9 setup display. If the date displayed is correct and does not need to be set, pressing mode 93 will display ECG 70 gain change menu shown in #7. If the date display is to be changed, pressing select 89 will present the display shown in #6C. The cursor appears under the first character capable of being changed. The advance 91 push-button will increment through the characters possible in each position and the select 89 button will move the cursor to the next character position. When the cursor reaches the last character, the next pressing of the select 89 button will move the cursor to the first-date character. When the date display is set correctly, pressing the mode 93 button will change the display to the ECG programs select display shown in #8. EGG gain change display will be seen if select 89 was pressed, as is shown in #7A.

The ECG gain change display for Holter shown #7A is changed by pushing the select 89 button. Compcorder™ 9 defaults to full gain with selection on subsequent screens for one-half ECG gain in each channel. ECG gain is used so that large EGG signals do not saturate the recording system. For normal size EGG signals and when the gain does not need to be changed, pressing the mode 93 button will bypass the ECG gain change screens, accept the default full gain and show the ready-to-record display #10C. If the ECG gain is to be changed, pressing the select 89 button will show the display seen in #7A. In the #7A display the arrow after the full indicates a channel is selected. If the advance 91 push-button is pressed, the arrow will move to the position just after the half shown in #7B indicating this is to be used. Pressing advance 91 again will move the arrow back to the full position shown in #7C. The position of #7C arrow when the select 89 button is pressed will determine the selection for the ECG gain of that channel. Pressing select 89 also moves to the ECG gain setting display for the next channel. When channel 3 has been set, the next pressing of select 89 will show a ready-to-record display #10C.

Selection of one or more of the various programs available including the recording of ECG may be made by using the pressing of mode 93 from display #8. The different programs that can be selected are shown in #8A through #10B; namely, ECG Holter, ECG/aristotle, ECG/LPA, ECG/pacer, ECG/BP, ECG/respiration and ECG/activity. This also depends on what plug and play signal conditioners 14 are resident in the Compcorder™ 9. If a particular program is selected and an associated signal conditioning unit 14 is installed, then it will be activated for the recording. If the specific signal conditioner 14 is not present, the program will not show on the display.

Selection of one or more of the various special programs that do not require the use of ECG 70 is made by again pressing mode 93 until the program of choice is selected as shown in #12A–13D; namely, temperature 80, conductance 84, esophageal 78, gas saturation 79, EEG 72, EMG 76 and EOG 74. Respective programs require that the associated plug and play signal conditioner 14 is installed in the Compcorder™ 9.

Compcorder™ 9 set-up menu for Holter recordings is accessed by pressing the mode 93 button when the ready-to-record display is shown which causes the Compcorder™ 9 set-up menu to be displayed as shown in #14. If the select 89 button is pressed while the ready-to-record button is displayed, the display will show the time format display #15B.

If the time format #15B is not to be changed, the mode 93 button is pressed to activate the beeper on/off display #15D. Pressing the select 89 button will display a time format selection display for a 24-hour clock or for an am/pm 12-hour clock. An arrow is moved by pressing the advance 91 button to be in the character position following the chosen time format. When the desired format is selected, pressing the mode 93 button will again show the beeper on/off display #15D.

The selection of beeper on/off control display to output an audible sound is seen in #15D. Advance 91 button will move the arrow to select 89 on or off on this display. After the desired selection is made, pressing the mode 93 button will show the selections for other programs depending on the input signal conditioning modules 14 selected or other internal operational programs such as pacer-store #9A for pacemaker pulse detection.

During Compcorder™ 9 set up the language selection display is shown when any of resident programs are selected from the menu. If a program such as pacer-store was exited, the language selection display shown in #15C appears. If the language used for the Compcorder™ 9 user interface is not to be changed, pressing the mode 93 push-button will show the resolution display #14A. To change the language used for the user interface, the select 89 button is pressed. A language selection display will appear. Pressing the advance 91 push-button will sequence through the available languages which typically consist of English, French, German, Italian and Spanish. When the desired language is on the display, pressing the mode 93 button will select this language and exit to the resolution display seen in #4A.

The resolution display is shown when exiting the language selection display #14A. If resolution is not going to be changed, pressing the mode 93 button will show the patient ID input display as seen in #3. The resolution can be changed by pressing the select 89 button. This will cause the resolution select 89 display to appear as shown in #14B for 8 bit-128 samples per second (s/s). Pressing the advance 91 button will cause the selection arrow to move through the three choices for 8 bit-128, 8 bit-256 or 12 bit-1024 samples per second. After selection of the desired resolution, the mode 93 button is pressed and the patient ID input display shown in FIG. 3 will appear.

The ready-to-record display #10C can now be accessed from the patient ID input display seen in #3 will appear after the last Compcorder™ 9 set-up display, beeper on/off control see in #15D, is exited. All of the Compcorder™ 9 initialization and set-up displays can be shown in sequence by continuing to press the mode 93 push-button. Any previous selection on these displays can be changed if the select 89 button is pressed at the appropriate display. Pressing the mode 93 button until the ready-to-record display shown in #10C appears then pressing select 89, will start the recording process, provided that the patient ID number has been changed since the battery 18 was last installed.

To end a recording the display #11B, press select 89 to end recording, is accessed at any time during a recording. During the recording of data, the time clock displays shown for a 12 or 24-hour clock is on the LCD 85 of the Compcorder™ 9. The arrow on the bottom line of the display moves continuously from left to right indicating the recording is in process. This time recording is terminated by pressing the mode 91 and advance 93 buttons simultaneously holding them down for five seconds. After holding them down for five seconds, the display shown in #11B appears. If select 89 is not pressed within five seconds, recording will continue and the LCD 85 will again show the time clock. If, while the display shown in #11B is on the LCD 85, the select 89 button is pressed, the display in FIG. #11C, "recording ended ok to pull media," will appear. Recording will terminate at this time and the display will remain as shown. The batteries 18 can be removed before or after the media is removed. If the above procedure is not followed and the batteries 18 or media are removed while the clock is on the LCD 85, up to ten minutes of data at the end of the recording will be lost.

Before the media is pulled, final selections are made for report output or other recorded data that is to be sent directly from the Compcorder™ 9 to other devices such as a printer, modem or fax station 108. This can be bypassed by a direct transfer of the recorded data using the RMM 16 to be moved from the Compcorder™ 9 to an external PC analyzer 24. Selection of the various output devices is shown in #16A–16E by pushing the mode 91 button to each selection after select 89 button is pushed. These selections can be made at the beginning or the end of a recording.

The signal conditioning module sensors (SCM) 14 are connected to the patient creating a signal that is amplified and conditioned then converted from an analog signal to a digital signal after which it is input to the micro processor module (MPM) 10. This includes various types of signal conditioning amplifiers, selected from types normally used in physiological monitoring of body signals, such as ECG 70, EEG 72, EOG 74, EMG 76, BP 86, Gastric & Esophageal pH 78, temperature of skin or body 80, respiration 82, skin conductance 84, pacemaker 88, gas saturation 79 and may include body sensors measuring physical activity, body and limb position 75, foot force 77, gas (oxygen/carbondioxide) saturation 79 and movement using acceleration 90 sensors.

Furthermore, each conditioner can have circuitry or preprocessing ability to enhance the signal prior to storage in the main memory module. Each conditioner can include absolute calibration signals that are inserted into the analog signal data flow from the sensor, at selected times and durations and at an amplitude in providing reference signals that would be useful to the user. This can include standard one millivolt pulses, singly, periodically or continuously for use in a Holter application where standard Holter analyzers use this signal before analysis of the ECG 70 is done. Similarly, other reference signals can be inserted in the analog signal amplifiers, consistent with the signals monitored, to ensure an absolute reference.

A brief description of twelve signal conditioning type modules follows, however, other types not described in this embodiment may also be connected to this device and stored into the RMM 16 described. The discussions are brief since this technology has become standard to those associated with the art of physiological monitoring and may depend on the experience and preference of the user, therefore the invention disclosed in this embodiment does not specifically relate to the body sensors and signal amplifiers.

Figure 9:
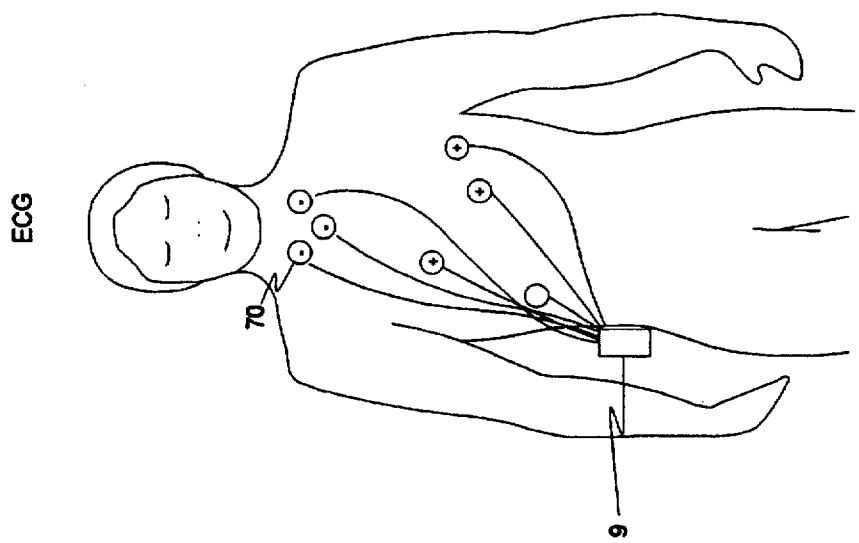
FIG. 9 is a diagram of electrocardiograph (ECG) sensor orientation.

ECG FIG. 9 shows a typical configuration for a Holter hook-up for ECG 70 measurement with leads to the signal conditioning amplifiers 14. The electrodes 70 are attached to the patient in a conventional arrangement as shown, usually with seven or five electrodes, that allow recording three channels. The first stage isolates the patient from the possibility of electric shock and prevents electrical signals or static to get into the recorder thereby preventing potential damage. Signal conditioning amplifiers and filters 14 prepare the analog signal for conversion to digital by the A/D converter 52. The input amplifier 14 includes inputs from the event switch and the calibration signal source. The calibration signal is input at the true input to ensure that this signal represents a value of one millivolt relative to the ECG signal. After further amplification and filtering the signals go to the A/D converter 52 then to the MPM 10. The A/D converter 52 is controlled by the MPM 10 relative to clock rate and resolution, which depends on the program being run for the Holter application. The system described is capable of clocking the signal through the A/D 52 at 256, 512 or 1024 samples per second (s/s). The resolution of the A/D converter 52 can be changed from 8 bit to 12 bit by the operational program using an output signal from the MPM 10. This is done to support the recording of high resolution signals that need an analog resolution of one part in 1024 rather than one part in 256 for an 8 bit conversion. This resolution of one part in 1024 is required to measure late potentials, which are very low signals, as low as one microvolt. A Del Mar/Cherry U.S. Pat. No. 5,205,295 describes a method of recording and analyzing Holter ECG 70 signals to determine late potentials, using a recording medium such as described in this embodiment.

Figure 10:
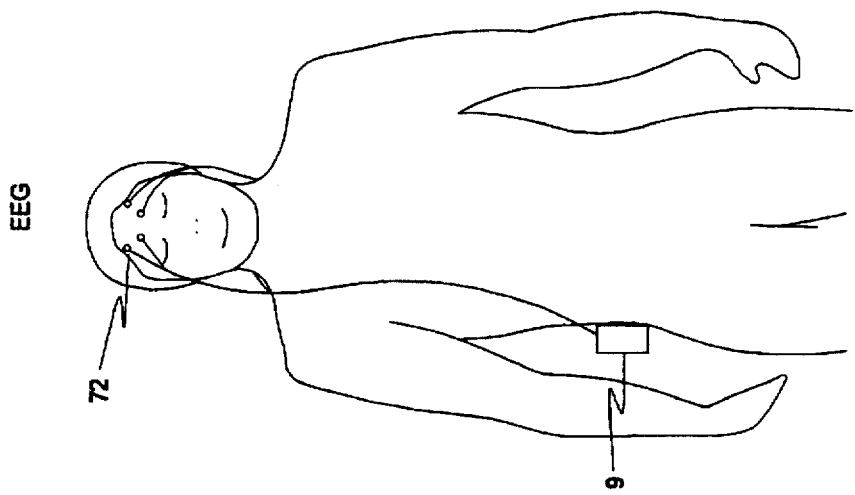
FIG. 10 is a diagram of electroencephalogram (EEG) sensor orientation.

EEG FIG. 10 shows the method of EEG 72 measurement of the brain, known as an electroencephalogram. This is similar to the more common ECG type of test except that the signals are of much lower signal amplitude and generally of higher frequency. Additional signal amplifiers, ahead of typical ECG inputs are usually required and data channels typically consist of at least seven channels 72. In a similar fashion to ECG, the signals are multiplexed by SCM 14 into the MPM 10 if other physiological monitoring efforts are in process.

Figure 11:
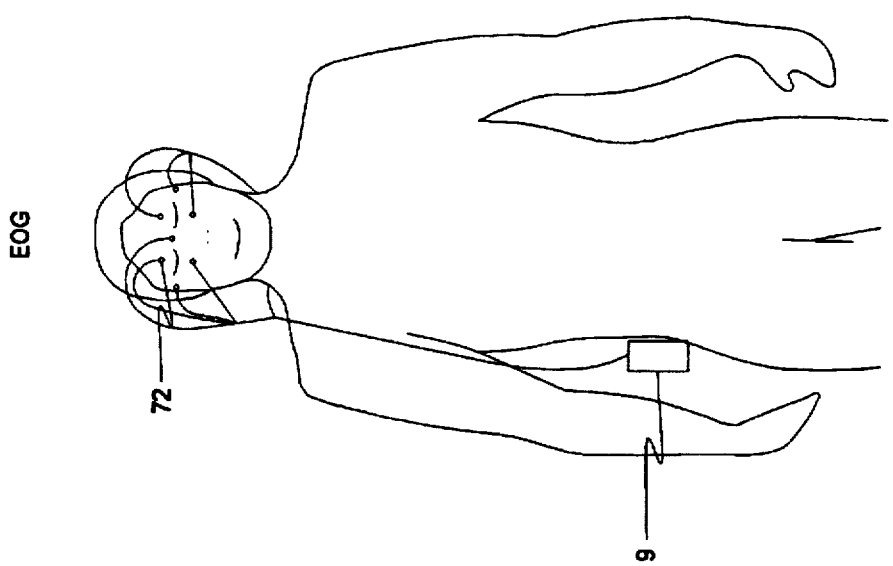
FIG. 11 is a diagram of electro-oculogram (EOG) sensor orientation.

EOG FIG. 11 shows a method to achieve an electro-oculogram (EOG) measurement of the eye. This is a test for the measurement of eye movements. This is done by special high-gain DC amplifiers and two electrodes near the eye. The electrodes must be of a type that does not generate self-induced voltages by contact with the skin and must be matched so that any self-induced voltages cancel out. The EOG is used to determine eye movements in sleep and dream (REM) studies and to evaluate reading ability and fatigue. Necessary amplifiers are DC coupled and are in low noise to condition signals to 50 Hz from signal levels as low as 50 microvolts. The two electrodes 72 are positioned above and below the eye to measure vertical eye movements and on the nose and temple for horizontal movements.

Figure 12:
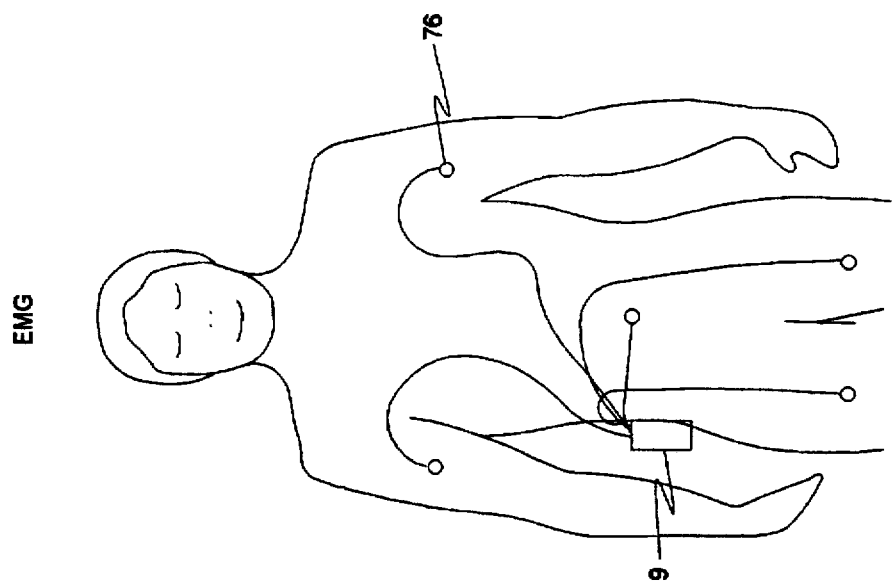
FIG. 12 is a diagram of electromyogram (EMG) sensor orientation.

EMG FIG. 12 shows the connections for an electromyogram (EMG) test. This is a test to measure muscle activity. Depending on the electrodes used, either surface or needle, the signal conditioner 14 used has to amplify signals with a frequency of 50 to 2000 Hz and from levels of 100 microvolts. The signal conditioner 14 amplifies the differential signals from the electrodes 76, then is multiplexed into the micro computer module 10 for storage on the removable memory module 16.

Figure 13:
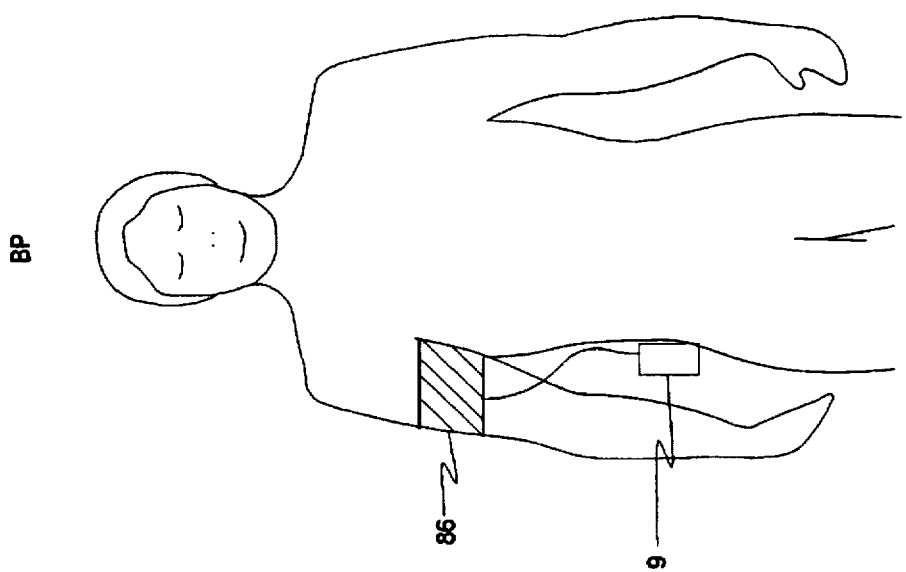
FIG. 13 is a diagram of blood pressure (BP) sensor orientation.

BP FIG. 13 shows a typical hook-up of an apparatus that is used in an ambulatory application, for the measurement of BP, over extended periods of 24-hours or more. This process has been previously described in Squires/Cherry U.S. Pat. No. 4,216,779 which recorded the data into a tape recorder rather than the RMM 16 described in this embodiment.

Figure 14:
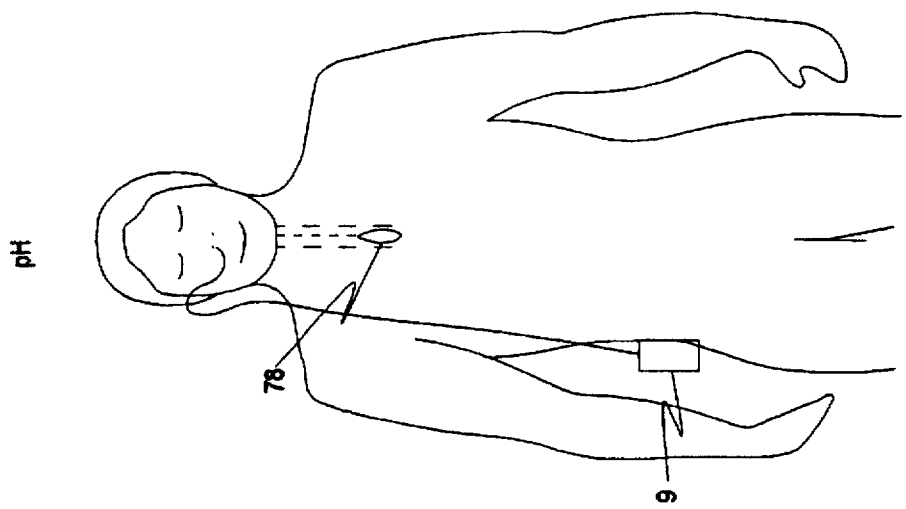
FIG. 14 is a diagram of esophageal (pH) sensor orientation.

Esophageal FIG. 14 shows measurement of pH relative to body acid or alkaline levels and has been a standard test in an ambulatory application since 1975. Measurement is made by the use of a glass electrode with the property of generating electrical potentials when placed in different pH solutions. The signal conditioner 14 shown amplifies the very low level signals generated with components from DC to 1 Hz. In this application the measurement of pH in the stomach of the human body is embodies. The glass probe is inserted down the throat to measure the pH levels of the liquids in the stomach over a range of 3–13 pH units. Calibration of the unit and probe is done by placing the probe in a standard solution with a known pH. The pH data is changed from an analog value to a digital value by the A/D converter 52 then processed by the MPM 10, then recorded on the RMM 16.

Figure 15:
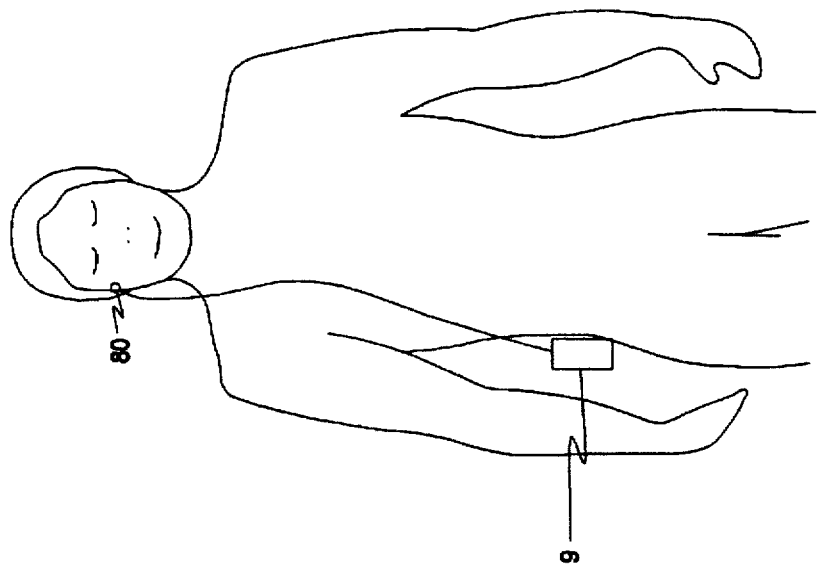
FIG. 15 is a diagram of temperature sensor orientation.

Temperature FIG. 15 shows a method for the measurement of temperature of the skin and body. Temperature is measured by the electrodes 80 and conditioning amplifiers 14 as illustrated. Skin temperature can be measured under a waist belt or ear lobe and body temperature by means of a rectal probe. Skin temperature is altered by blood flow and shows a patients anxiety. Body temperature measurements show the state of health but may also show changes related to exercise and cooling.

Figure 19:
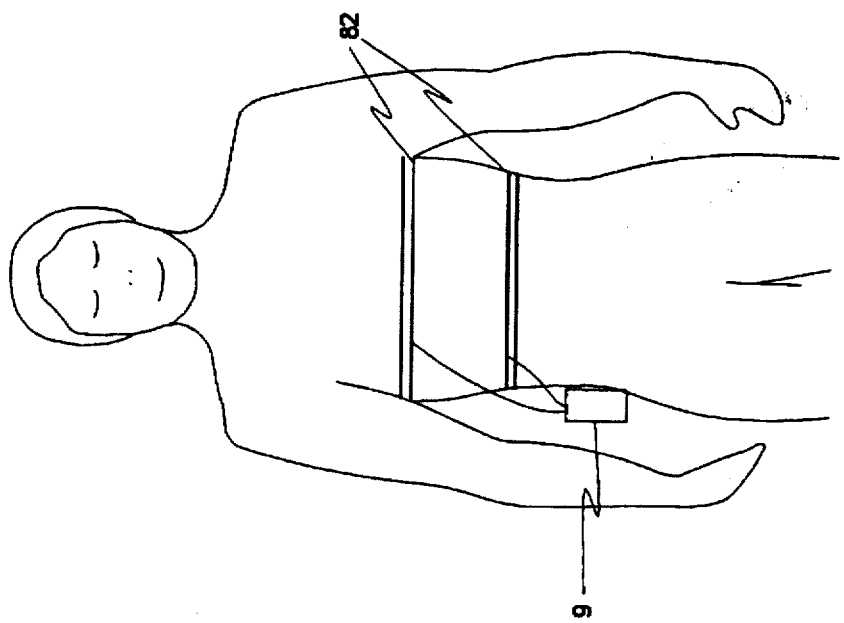
FIG. 19 is a diagram, of respiration sensor orientation.

Respiration FIG. 19 shows the signal conditioning block for the determination of respiration rate and effort. Respiration is frequently associated with anxiety; changes affect skin conductance and heart rate. Respiration rate can also be measured by standard impedance plethysmograph methods and circuits which use ECG electrodes 82 attached to the thorax in a bridge circuit or by the use of a stretchable band around the chest. The respiration signal is separated from the Ecg signals by filters that only pass signals in the bandpass of 0.03–6 Hz. The output signal is then multiplexed by SCM 14 into the MPM 10.

Figure 16:
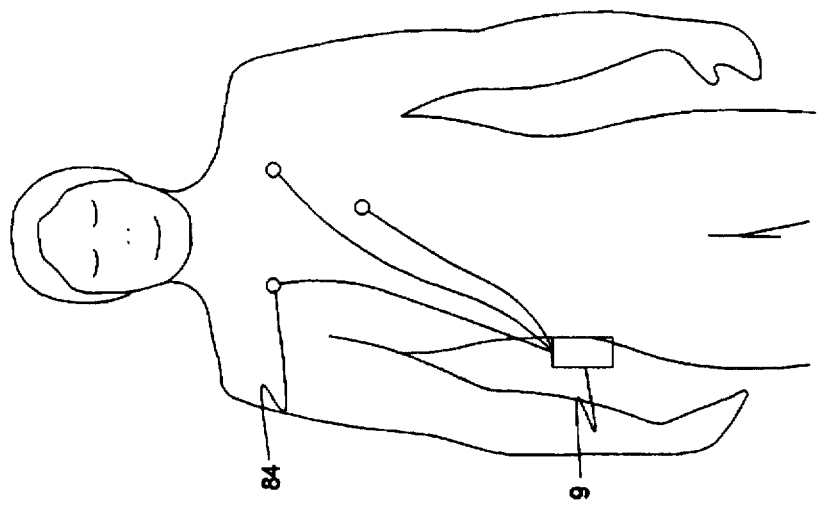
FIG. 16 is a diagram of skin conductance sensor orientation.

Conductance FIG. 16 shows a typical diagram for the measurement of skin conductance and response. The galvanic skin response is used as a quantitative measure of autonomic activity as a result of stress. A change results from an increase in sweat gland activity or from a vascular change in blood flow. Temperature also changes skin conductance along with the electrolyte used on the conducting electrodes. The diagram shows three electrodes 84 connected to the chest and amplifier then multiplexed by SCM 14 to the MPM 10. The resultant signals are then stored in the RMM 16 for later analysis by an external computer 24.

Figure 17:
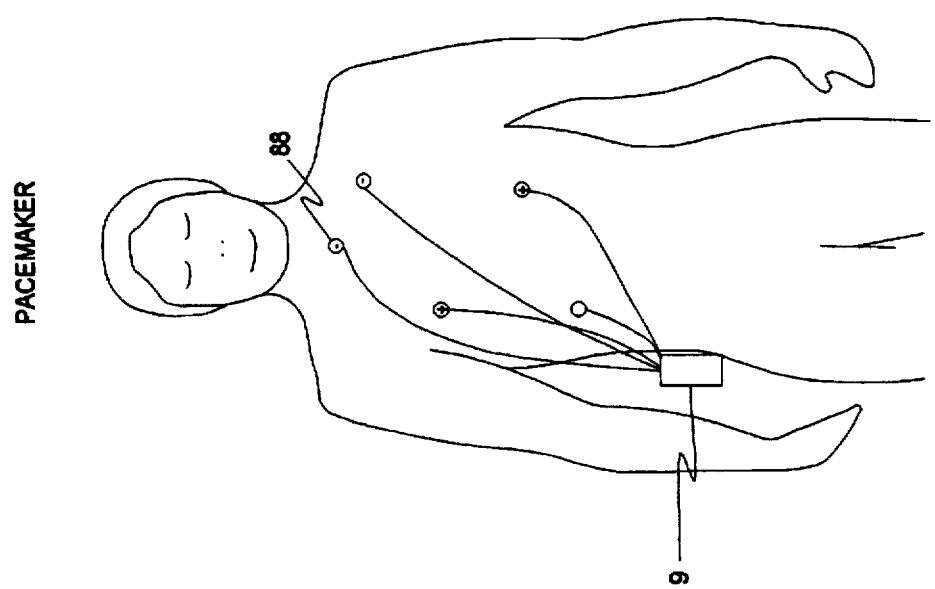
FIG. 17 is a diagram of pacemaker sensor orientation.

Pacemaker FIG. 17 shows the signal conditioning for the detection of voltage spikes from a pacemaker. The signals from the ECG electrodes 88 shown are separately amplified and conditioned to enhance the detection of cardiac pacemaker spikes to determine a time relationship relative to each ECG "R" wave and to generate a synthesized signal that could be easily identified in an ECG tracing. A method of detection and recording of pacemaker spikes has been previously disclosed by Kelen in U.S. Pat. No. 4,291,703. This embodiment is similar to the detection of the pacemaker spikes as shown in said patent however, after detection, a signal goes to MPM 10 that it is then time related to real time with a resolution to enable a later match in time to the specific ECG signals and "R" waves being recorded. The subsequent pacemaker conditioned signal spike, time-of-day, record of each spike for this embodiment is stored in digital form on the RMM 16 rather than tape as a synthesized pulse as defined in said patent.

Figure 18:
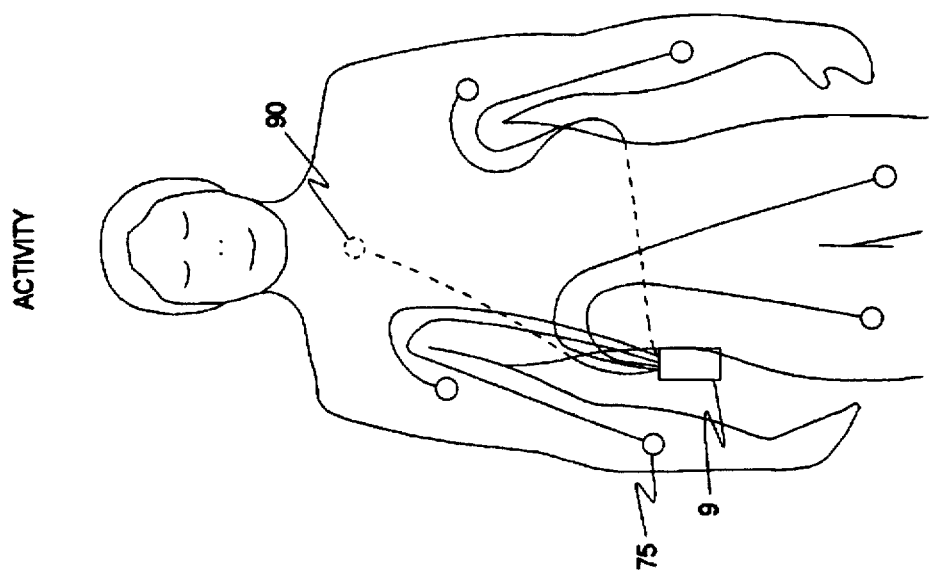
FIG. 18 is a diagram of activity, body limb accelerometer sensor orientation.

Activity FIG. 18 shows the kinetic activity monitor signal conditioning. The main feature of such a device is to augment Holter ECG 70 by monitoring the body to quantify and display the body position 75 and motion 90, that a patient experiences. The position of the torso is monitored and if horizontal is interpreted as the patient lying down or sleeping. If the body is vertical, then the amount of motion detected by the body is quantified and recorded into the removable memory module 16 along with the position. When the torso is vertical, a person may be standing, walking, running or sitting. This type of device and the analysis of the data has been covered in Thornton including U.S. Pat. Nos. 4,830,021, 4,993,421, 5,036,856, 5,125,412 referenced here for further reading and understanding. As shown in the diagram the signals from the two position sensors 75 are conditioned and multiplexed with the acceleration sensor 90 into the micro processor module 10. Absolute calibration signals may be induced into the activity signal train, by hand dropping the "g" sensor a short distance in free fall through the air, thus creating a gravity signal transitioning from 1g to 0 g and back again, thus calibrating one "g". However, it is not an essential ingredient of this invention to use calibration signals or to use a kinetic activity monitor generated signal as described herein. The activity data and body/foot force 77 stored in the removable memory module 16 is transferred to a standard computer 24 for viewing and in some cases printout in conjunction with other transducer signals and Holter ECG 70.

The above description is intended to enable any person skilled in the art of physiological or Holter monitoring of an ambulatory patient, to construct and use the present invention as disclosed herein, and details the best mode and features known to the inventor, to reproduce and use the invention. Various alternate signal conditioning functions and storage media will become available in the future and their use will be obvious to those skilled in the art, it is therefore possible that the invention may be practiced by means other than those specifically disclosed herein.

Figure 20:
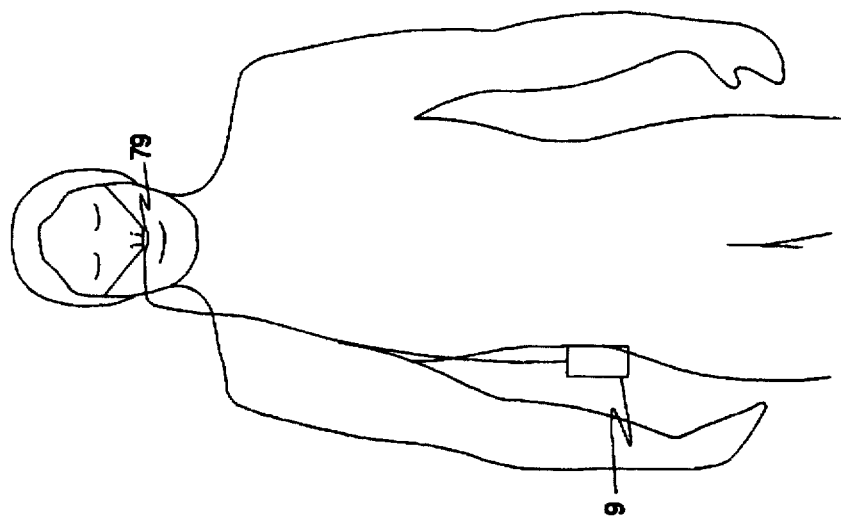
FIG. 20 is a diagram of gas saturation and volume sensor orientation.

Gas saturation and volume measurement methods are shown in FIG. 20. Analysis of the composition of gas mixtures in respiratory studies is one of the primary methods of obtaining information about lung function. Sensors with fast response times have been developed for the continuous measurement of interbreath events and the measurement of $O_2/CO_2$ concentrations. These sensors are applied to the air passages of a patient as shown.

What is claimed is:

1. A computer-recorder for ambulatory, real time data analysis and data accumulation of a variety of biophysical, biomechanical and physiological somatic data of a patient, comprising:

a central processor unit (CPU) assembly housing having a plug and play micro processor module (MPM) disposed therein;

at least one, self-contained, plug and play power module (PM) insertable into said CPU;

at least one plug and play system operation and data-analysis, control program module (CPM) insertable into said CPU and coupled to said MPM;

at least one set of plug and play biophysical, biomechanical and physiological sensors for attachment to said patient;

at least one plug and play, data input signal conditioner module (SCM) insertable into said CPU assembly housing and coupling at least one set of said sensors to said MPM;

at least one plug and play data storage removable memory module (RMM) insertable into said CPU assembly housing and coupled to said MPM;

at least one interactive user control module (UCM) disposed on said assembly housing and coupled to said MPM; and at least one plug and play output port disposed in said CPU assembly housing and coupled to said MPM.

2. A computer-recorder according to claim 1, wherein said CPM couples a patient identification code and related patient demographic data to a specific set of said patient data accumulated and stored in said RMM.

3. A computer-recorder according to claim 1, wherein said CPM is an electronically erasable and programmable read only memory (EEPROM).

4. A computer-recorder according to claim 1, wherein said SCM functions to manifest an implanted pacemaker pulse detector.

5. A computer-recorder according to claim 1, wherein said SCM functions to manifest an electrocardiograph (ecg).

6. A computer-recorder according to claim 1, wherein said SCM functions to manifest an electromyogram (emg).

7. A computer-recorder according to claim 1, wherein said SCM functions to manifest an electroencephalogram (eeg).

8. A computer-recorder according to claim 1, wherein said SCM functions to manifest an electro-oculogram (eog).

9. A computer-recorder according to claim 1, wherein said SCM functions to monitor an esophageal pH.

10. A computer-recorder according to claim 1, wherein said SCM functions to monitor blood pressure.

11. A computer-recorder according to claim 1, wherein said SCM functions to monitor foot force.

12. A computer-recorder according to claim 1, wherein said SCM functions to monitor body and limb angular orientation.

13. A computer-recorder according to claim 1, wherein said SCM functions to monitor skin temperature.

14. A computer-recorder according to claim 1, wherein said SCM functions to monitor skin conductivity.

15. A computer-recorder according to claim 1, wherein said SCM functions to monitor respiration.

16. A computer-recorder according to claim 1, wherein said SCM functions to monitor oxygen/carbon dioxide saturation.

17. A computer-recorder according to claim 1, wherein said SCM functions to monitor body/limb acceleration.

18. A computer-recorder according to claim 1, wherein said plug and play RMM is of the size and electronic configuration that is interchangeable with a conventional PCMCIA format and is therefor adaptable to and insertable in a multitude of personal computers and related equipment.

19. A computer-recorder according to claim 18, wherein said RMM is a non-volatile memory.

20. A computer-recorder according to claim 19, wherein said RMM utilizes magnetic tape as a storage medium.

21. A computer-recorder according to claim 19, wherein said RMM utilizes magnetic disc as a storage medium.

22. A computer-recorder according to claim 19, wherein said RMM utilizes a solid-state/integrated circuit device (flash card) as a storage medium.

23. A computer-recorder according to claim 19, wherein said RMM utilizes a laser disc/optical disc as a storage medium.

24. A computer-recorder according to claim 19, wherein said RMM utilizes a laser card/optical card (OC) as a storage medium.

25. A computer-recorder according to claim 19, wherein said RMM utilizes a laser tape/optical tape as a storage medium.

26. A computer-recorder according to claim 1, wherein said output consists of at least two output ports, at least one of which is a serial port.

27. A computer-recorder according to claim 26, wherein said output consists of at least one parallel port.

28. A computer-recorder according to claim 27, wherein said parallel port may be configured to couple directly to a printer for both a full-disclosure printout and also a printout of analyzed data.

29. A computer-recorder according to claim 27, wherein said parallel port is configured to link said computer-recorder directly to a PC to output data from said computer-recorder and to program said CPM.

30. A computer-recorder according to claim 26, wherein said serial port is configured to couple to a modulator/demodulator (modem) for transmission over a telephone line.

31. A computer-recorder according to claim 26, wherein said serial port is configured to couple directly to a facsimile machine (fax) over a telephone line.

32. A computer-recorder according to claim 26, wherein said serial port is configured to couple directly to a personal computer (PC) over a telephone line.

33. A computer-recorder according to claim 32, wherein said PC is enabled to communicate directly with said CPU for data input and output, and to program said system operation and said data analysis CPM.

* * * * *